(12) United States Patent
Kasai et al.

(10) Patent No.: US 6,805,784 B2
(45) Date of Patent: Oct. 19, 2004

(54) CAPILLARY ARRAY

(75) Inventors: Syozo Kasai, Hitachinaka (JP); Kiyoshi Tsukada, Mito (JP); Toshiaki Kita, Hitachinaka (JP); Tomonari Morioka, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 246 days.

(21) Appl. No.: 09/797,698

(22) Filed: Mar. 5, 2001

(65) Prior Publication Data

US 2001/0047942 A1 Dec. 6, 2001

(30) Foreign Application Priority Data

May 15, 2000 (JP) ........................................ 2000-147498

(51) Int. Cl.⁷ ........................ G01N 27/453; G01N 30/02
(52) U.S. Cl. ........................ 204/601; 422/70; 204/601; 204/605
(58) Field of Search .................... 422/70; 204/451–455, 204/601–605

(56) References Cited

U.S. PATENT DOCUMENTS

| 5,274,240 A | 12/1993 | Mathies et al. |
| 5,366,608 A | 11/1994 | Kambara |
| 5,439,578 A | 8/1995 | Dovichi et al. |
| 5,516,409 A | 5/1996 | Kambara |
| 5,529,679 A | 6/1996 | Takahashi et al. |
| 5,582,705 A | 12/1996 | Yeung et al. |
| 5,730,850 A | 3/1998 | Kambara et al. |
| 5,759,779 A * | 6/1998 | Dehlinger ...................... 435/6 |
| 5,790,727 A | 8/1998 | Dhadwal et al. |
| 5,900,132 A * | 5/1999 | Keenan et al. ............... 204/603 |
| 6,270,644 B1 * | 8/2001 | Mathies et al. .............. 204/603 |

FOREIGN PATENT DOCUMENTS

JP 9-96623 4/1997

\* cited by examiner

*Primary Examiner*—Alex Noguerola

(57) ABSTRACT

The structure of a capillary head section is made such that the liquid contacting surfaces of a capillary holder, a capillary, and an adhesive form a plane surface, and this shared liquid contacting surface is made a mirror surface with a surface roughness of 3.2 s or less. In the shared liquid contacting surface, the ratio of the total area of the capillaries to the internal diameter area of the capillary holder is made 60 to 73%.

42 Claims, 3 Drawing Sheets

CAPILLARY ARRAY

BACKGROUND OF THE INVENTION

1. Field of the Invention

The present invention relates to capillary arrays used in capillary array electrophoresis equipment that separates and analyzes samples such as DNA, proteins, etc.

2. Description of Prior Art

The technology is well known of configuring an array by combining a plurality of capillaries, supplying to each capillary and moving electrophoresis medium and the sample to be separated or analyzed, and using the target sample for carrying out separation or analysis. The samples such as DNA, protein, etc., that are labeled by fluorescent materials are supplied to the capillaries. Such technology has been disclosed in U.S. Pat. Nos. 5,366,608, 5,529,679, 5,516,409, 5,730,850, 5,790,727, 5,582,705, 5,439,578, and 5,274,240, etc. From the point of view of the throughput of separation and analysis, the method using multiple capillaries has many advantages compared with the electrophoresis method using a flat plate gel.

A capillary array electrophoresis equipment has been disclosed in JP A 9-96623. The capillaries have an external diameter of 0.1 to 0.7 mm, an internal diameter of 0.02 to 0.5 mm, with the outer covering being a Polyimide resin coating. Each capillary itself is quartz pipe, with a number of capillaries in the array (generally, a few to several tens of capillaries are common.).

This equipment is provided with a loading head that takes the DNA into the capillary by electrophoresis from the sample tray containing DNA sample labeled by a fluorescent material, an excitation optical system that irradiates excitation light beam from electromagnetic waves, for example, the laser light source via the mirror, beam splitter, and focusing lens to the detection sections that are arranged and fixed in the order of the sampling number of the loading header, and a detection lens system and CCD camera that detect the fluorescence light which is the signal light. In this example, laser light is irradiated from both side surfaces of the capillary array containing the electrophoretic DNA, focusing the laser light by the lens effect of the capillary, thereby irradiating all the capillaries with laser light, and detecting the fluorescent light from each capillary using the detection optical system.

SUMMARY OF THE INVENTION

An object of the present invention is related to the structure of the capillary head section, and to eliminate air bubble generated when a gel is introduced, and also to ensure that there is no adherence of air bubbles to the liquid surface.

The present invention relates to capillary arrays used in capillary array electrophoresis equipment that separates and analyzes samples such as DNA, proteins, etc., and in particular to the prevention of air bubble generation at the capillary head section of the capillary array and to the improvement of the sealing construction.

In more detailed terms, the present invention divides the capillary head into three parts of the pipe-shaped capillary holder 32, the sealing peg 33, and the tightening knob 34. Because of this, even when the tightening knob is rotated, the sealing surface that maintains the hermeticity does not rotate but only the sealing pressure is applied. The capillaries are bundled together, passed through the capillary holder, and adhered together, the capillaries and the capillary holder are cut simultaneously so that they are in the same plane. Further, the roughness of the surfaces of the capillaries and the capillary holder in the same plane is made so that the surfaces each have an approximately mirror-finished surface.

According to other preferred embodiments, in the shared plane of the capillaries and the capillary holder, the internal diameter area of the capillary holder is made so that the capillary filling rate becomes 60 to 73% indicating the ratio of the area of the capillaries and the adhesive surface to the internal diameter area of the capillary holder. Because of the above, there is no generation of craters appearing in the cut surface because voids are introduced in the adhesive material during the adhesion of the capillary head. In addition, since there are no undulations in the liquid contacting surface, it has been possible to eliminate the adhesion of air bubbles to that surface.

In the present invention, the hardness of the capillary holder, of the tightening knob, and of the buffer liquid container is larger than the hardness of the sealing peg. The area of the surface of contact between the capillary holder and the sealing peg is made larger than the area of the surface of contact between the sealing peg and the tightening knob. Further, electrophoresis is carried out by applying a voltage of about 10 to 20 kV from the high voltage power supply between the electrode attached to the capillary front tip of the loading header and the electrode provided in the buffer liquid container that injects the buffer liquid, which is the electrophoretic medium in the capillary, from the capillary head into the detection section. The capillaries, the loading header, the electrodes, the detection section, and the capillary head part prepared in an integrated manner are called the capillary array on the whole. The attaching and detaching of the capillary array are done as a single unit. Further, gel has been introduced inside the capillary that becomes the resistance to electrophoresis, the speed of electrophoresis changes depending on the size of the electrophoretic DNA or protein molecule.

The detection time t (called the electrophoresis time) of this detection system is given by the following equation:

$$t = \frac{KL}{ET}$$

Where,
k: Proportionality constant
E: Electrophoresis voltage
L: Length of the capillary
T: Ambient temperature.

The detection time of the equipment at present is generally very long being in the range of 0.5 to 3 hours.

From the temporal variation pattern of the detection light intensity obtained from the above equation, the analysis of the DNA or the protein is done by the signal processing and computation equipment. However, the resolution of the signal pattern varies due to different factors, and in particular, the effect of the temperature changes of the equipment is large. One such example is explained below in detail. When injecting a gel in the capillary array, the high viscosity gel put in the buffer liquid container is applied a high pressure of 5 to 10 MPa using a pump, etc., thereby injecting the gel into the capillary. The completion of gel injection can be confirmed when the gel comes out from the electrode section. The injecting pressure is large because the viscosity of the gel is high and the internal diameter of the capillary is small. After injecting the gel, the buffer liquid for causing electrophoresis inside the gel is made to permeate from the buffer liquid container and from the electrode side of the loading header. In this type of analyzing equipment, the following problems will be generated if air bubbles are included in the part filled with the gel.

(1) If an air bubble with a diameter larger than the internal diameter of the capillary is injected into the capillary, the conduction of electricity inside the capillary will be cut off making electrophoresis impossible and hence the analysis also becomes impossible.

(2) While the capillary head is mounted in the buffer liquid container or affixed to the buffer liquid container at the high-pressure resisting and hermetic sealing part, if an air bubble is present in the vicinity of the mounting part 30, the volume of the air bubble changes due to the system temperature changes during analysis, and the buffer liquid comes out and goes back in via the capillary at the open end which is the electrode end. The amount of buffer liquid coming out and going back in will be different for each capillary because there will be differences in the pressure loss. Since this increases or decreases the time taken for electrophoresis, it will have direct effect on the analysis. The number 26 refers to the adhesive material that bonds the bundle of capillary tubes to the capillary head.

Because the above problems are present, the high-pressure resisting and hermetically sealed structure of mounting the capillary head to the buffer liquid container has been given the utmost care.

Because of the above, even when tightening is done by rotating the tightening knob, the capillary holder and the sealing peg do not rotate, and it becomes possible to prevent the sealing surface from being scratched, thereby obtaining a perfect seal.

PREFERRED EMBODIMENTS OF THE INVENTION

In the following, the preferred embodiments of the present invention are described referring to the figures.

An embodiment will be described hereunder.

Figure 1:
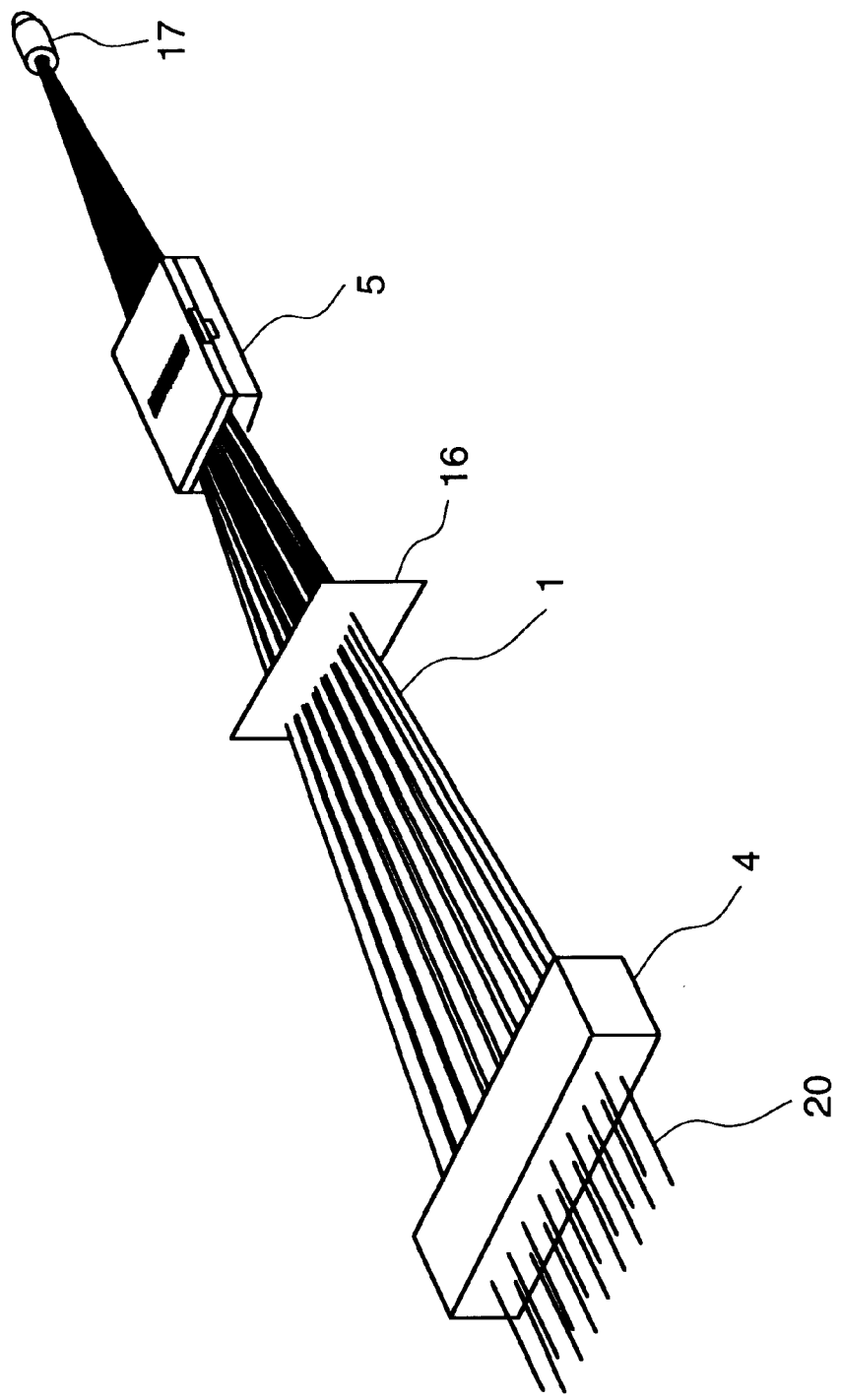
FIG. 1 is an overall pictorial view of the structure of a capillary array according to the present invention.

FIG. 1 shows a capillary array according to the present invention. A plurality of capillaries 1 having polyimide or other covering are bundled together to form an array of capillaries. The covering of the capillaries in the detector section 5 are removed making the capillaries transparent. A capillary separator 16 supports the capillaries so that each capillary is separated from its neighboring ones by a specific distance without collecting in one location and there is no concentration of heat generated due to electrophoresis. In order to cause electrophoresis, the sample supply section of the capillaries is connected to the loading header 4, which is one of the electrodes for the electrophoresis voltage to be applied. The sample supply section has an electrode 20 that is electrically connected to the loading header 4. The gel and the buffer liquid are supplied to the capillary head 17, and the assembly part of the capillary head is present in the buffer liquid container.

Figure 2:
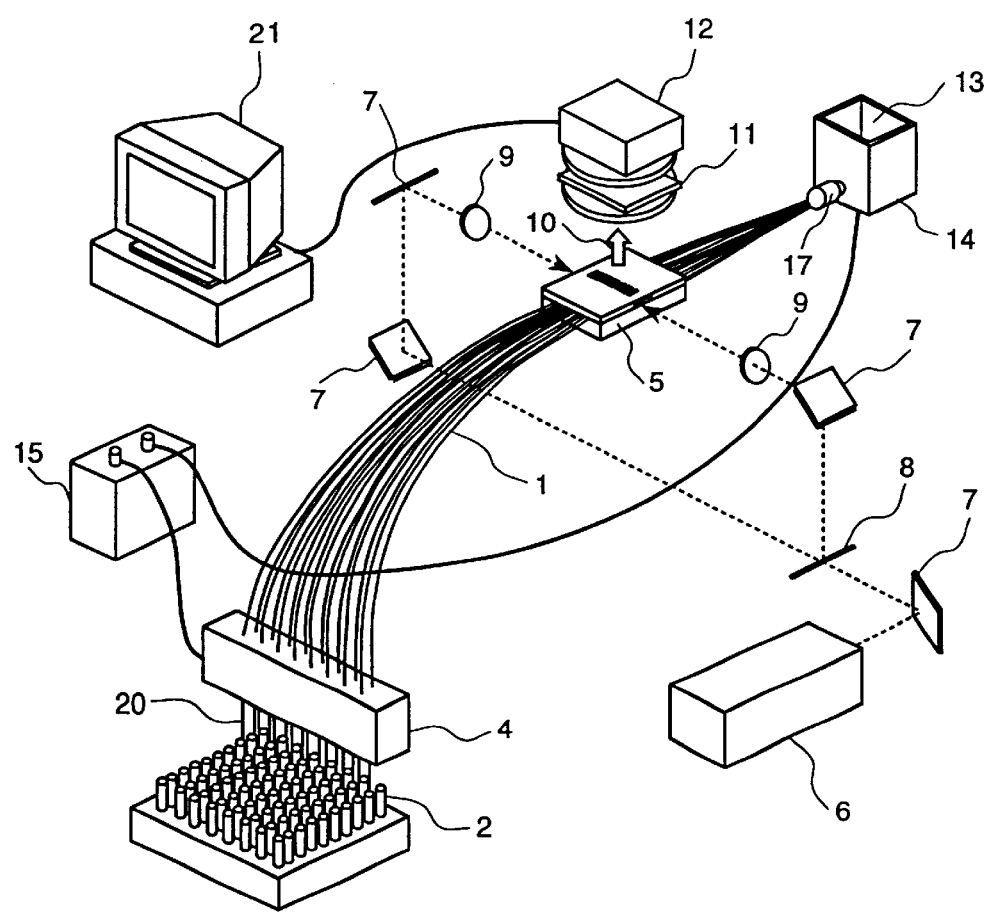
FIG. 2 is an outline diagram showing the electrophoresis equipment system applicable to the present invention.

FIG. 2 shows the electrophoresis system applicable to the present invention, and the sample supply section of the capillary is inserted in the sample containers 2. A voltage from the power supply 15 is applied between the loading header 4 and the capillary head 17 of the capillary array, and the sample that is labeled by the fluorescent dye in the capillary is separated in the order of the molecular weights.

The laser light (shown by dotted line in FIG. 2) generated by the laser source 6 is reflected by the mirror 7, split into two equal intensity beams by the beam splitter 8, and is irradiated onto the detection section 5 of the capillary array from both sides via the mirror 7 and the focusing lens 9.

The fluorescent light 10 that is generated is detected by the CCD camera 12, etc., via the detector lens 11. This detection signal is subjected to the necessary processing in the signal processing and computation equipment 21, and the necessary data is output and displayed.

Figure 3:
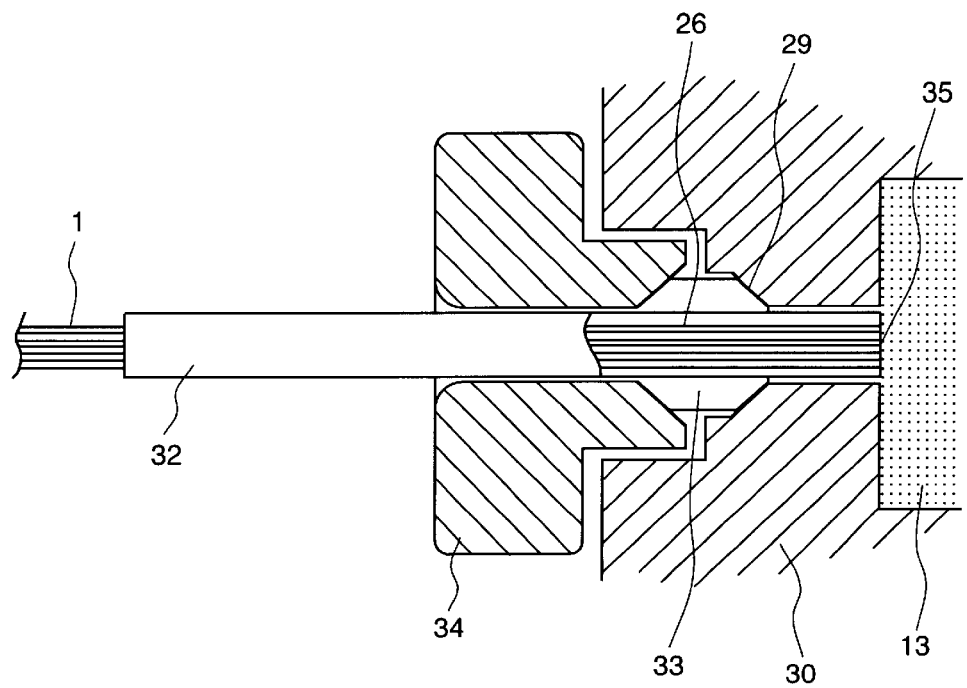
FIG. 3 is a cross-sectional view showing the detailed construction of the array head part of the capillary array according to the present invention.
Figure 4:
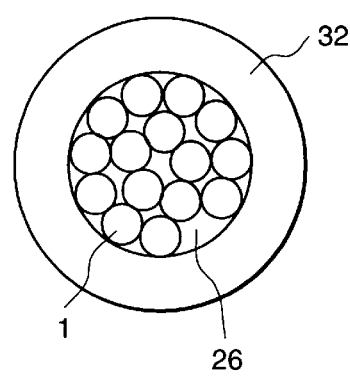
FIG. 4 is a cross-sectional view showing the construction of the capillary array head of FIG. 3.

As is shown in FIG. 3 and FIG. 4, the capillary head 17 is divided into the three parts of the capillary holder 32, sealing peg 33, and the tightening knob 34, and ten or more capillaries 1 are bundled together and incorporated in the capillary holder 32. At the front end part 35 of the capillary holder, the capillaries and the capillary holder are bonded together using an adhesive and are cut in a direction perpendicular to the longitudinal direction of the capillaries. All the three parts form the same plane and are incorporated into the buffer liquid container 14 containing therein buffer liquid 13. The cutting is done using a diamond saw so that the cut surface becomes a mirror surface with a surface roughness of 3.2 s or less so that even if air bubbles get attached to the cut surface, they can be taken out easily. The condition of cutting is that the rotational speed of the diamond saw is, for example, about 20,000 rpm.

Another preferred embodiment of the present invention is described below using FIG. 3. The present invention is related to the hardness of the high-pressure resisting and hermetically sealed part or of the different components and to the contact surface area. While the high-pressure resisting and hermetically sealed part is subjected to the necessary surface pressure at the contacting component surface, since, in the conventional equipment with screw tightening, the surface pressure was being increased while the contacting surface was rotating, the contacting surfaces were causing scratches on each other thereby losing the sealing performance. In addition, when attaching and detaching are repeated, friction dust generated which got trapped between the sealing surfaces thereby hindering the sealing performance.

In the present preferred embodiment of the invention, the capillary head was divided into three components. The contacting surface between the capillary holder 32 and the sealing peg 33 is made larger than the contacting surface between the sealing peg and the tightening knob so that even when the tightening knob is rotated, only a force in the axial direction is applied to the sealing peg 33 and no rotational force is applied to it. By doing this, the frictional resistance of the tightening knob becomes smaller than the frictional resistance of the capillary holder, and even when the tightening knob is rotated, there is no possibility of the sealing surface rotating. Furthermore, by making the hardness of the capillary holder, the tightening knob, and of the buffer liquid container larger than the hardness of the sealing peg, the sealing peg gets closer to the contacting surface when the sealing surface pressure increases thereby further increasing the sealing performance.

Further, when the capillary head is incorporated, if the configuration is such that the edge part of the capillary holder projects towards the outside of the edge part of the tightening knob, at the time of injecting the gel or the buffer liquid into the capillaries, the air in the groove generated on the periphery of the capillary holder is ejected outside the system along with the liquid from the gap between the tightening knob and the capillary holder by loosening the high-pressure resisting and hermetically sealing part, but there is no possibility of the capillary being dirtied by the liquid at this time.

The structure of the capillary holder according to the present invention is described below referring to FIG. 4. Conventionally, since a number of capillaries 1 are merely passed through the capillary holder 32, the internal diameter of the capillary holder had sufficient margin compared to the bundle of capillaries. As a consequence, even the amount of adhesive used was large. As an index of the degree of margin when the bundle of capillaries is inserted in the capillary holder is the capillary filling rate, which is the ratio of the sum S2 of the cross-sectional areas of all the capillaries included to the internal diameter area S1 of the capillary holder, that is $S2/S1 \times 100$ (%). This capillary filling rate is explained further below.

The conventional filling rate is 45 to 55% with the share of the adhesive is about 50%, and the voids contained in the adhesive or that get adhered to the capillary cause craters with a size roughly equal to the thickness of the capillary in the cut surface. Since it is difficult for the liquid to enter into such fine holes, air bubbles were being generated when the buffer liquid or the gel was injected, and also there was the problem that the air bubbles generated get into close contact with the hole and could not be removed from the system. Such air bubbles may also get detached from the hole due to some shock and enter into the capillary. As a method of countermeasure against such phenomenon, it is effective to increase the filling rate of the capillary thereby decreasing the ratio of the adhesive. According the experiments conducted so far, it became clear that when the filling rate exceeds 60%, the share of the adhesive decreases, and each adhesive cross sectional area becomes smaller than the air bubble area, and when the adhesive contained in a container is coated on the bundle of capillaries in a dipping method and removed, the air bubbles float up to the surface of the adhesive, and when the excess adhesive is removed at the capillary holder, even the air bubbles get removed along with the adhesive. When the filling rate exceeds 70%, although the generation of craters gets reduced further, it becomes difficult to insert the bundle of capillaries into the capillary holder.

When inserting about 10 to 30 capillaries, if considerations are given also to the drilling inside the internal diameter of the capillaries and to the nominal tolerance of the capillary external dimensions, it was found that the maximum filling rate is about 73% in order to manufacture in a stable manner. By doing this, the effect of air bubbles can be eliminated, the separation and analysis can be done with a high resolution and a high reliability, and also it was possible to obtain a seal structure with no leakage.

According to the present invention, it was possible to obtain a capillary array with no adhesion or generation of air bubbles in the analysis system, and with high-pressure resistance and excellent hermetic sealing performance.

The present invention relates to capillary array electrophoresis equipment that separates and analyzes samples such as DNA, proteins, etc., and in particular to the air bubble generation and sealing structure improvement of the capillary head part of the capillary array.

What is claimed is:

1. A capillary array for separating a sample into molecular species thereof comprising:
    a plurality of capillaries having first aligned ends and second aligned ends;
    a detection section arranging and holding said capillaries which are irradiated with electromagnetic waves;
    a plurality of sample injection inlets at the first aligned ends of the capillaries; and
    a capillary head for injecting an electrophoresis medium at the second aligned ends of the capillaries, wherein
    the aligned second ends of the plurality of capillaries are adhered to each other with adhesive, and a capillary holder having an end bundles the aligned second ends of the plurality of capillaries so that the capillary holder end, the aligned second ends of the plurality of capillaries, and the adhesive adhering the aligned second ends of the capillaries form a plane surface that will contact the electrophoresis medium.

2. A capillary array for separating a sample into molecular species thereof according to claim 1, wherein the plane surface formed by the capillaries, capillary holder and adhesive is an approximately mirror-finished surface.

3. A capillary array for separating a sample into molecular species thereof according to claim 2, wherein the mirror-finished surface roughness is 3.2 s or less.

4. A capillary array for separating a sample into molecular species thereof according to claim 1, wherein the electrophoresis medium comprises a gel and/or a buffer liquid.

5. A capillary array for separating a sample into molecular species thereof comprising:
    a plurality of capillaries having first aligned ends and second aligned ends;
    a detection section arranging and holding said capillaries which are irradiated with electromagnetic waves;
    a plurality of sample injection inlets at the first aligned ends of the capillaries; and
    a capillary head for injecting an electrophoresis medium at the second aligned ends of the capillaries, wherein
    the capillary head comprises a capillary holder that bundles together the second aligned ends of the capillaries; the capillaries are adhered together with adhesive; the second aligned ends of the capillaries, an end of the capillary holder, and the adhesive together form a plane surface for contacting the electrophoresis medium to be injected into the capillaries; and at the electrophoresis medium contacting surface the ratio of the total cross-sectional area of the capillaries in the bundled capillaries to the capillary holder internal diameter area is 60 to 73%.

6. A capillary array for separating a sample into molecular species thereof according to claim 5, wherein the electrophoresis medium comprises a gel and/or a buffer liquid.

7. A capillary array for separating a sample into molecular species thereof comprising:
    a plural number of capillaries having first aligned ends and second aligned ends;
    a detection section arranging and holding said capillaries which are irradiated with electromagnetic waves;
    a plurality of sample injection inlets at the first aligned ends of the capillaries;

an electrophoresis medium container adjacent to the second aligned ends of the capillaries; and a capillary head for injecting the electrophoresis medium from said electrophoresis medium container at the second aligned ends of the capillaries, wherein the second aligned ends of the capillaries are adhered to each other with adhesive and the capillary head has a capillary holder that bundles together the second aligned ends of the capillaries, the capillary holder being sealed and fixed using a sealing peg and a tightening knob, and the hardness of each of said capillary holder, of said tightening knob, and of said electrophoresis medium container is greater than the hardness of said sealing peg.

8. A capillary array for separating a sample into molecular species thereof according to claim 7, wherein the capillary holder contacts the sealing peg to form a first contact area, and the sealing peg contacts the tightening knob to form a second contact area, and the first contact area is larger than the second contact area.

9. A capillary array for separating a sample into molecular species thereof according to claim 5, wherein the capillary holder is longer than the tightening knob.

10. A capillary array for separating a sample into molecular species thereof according to claim 7, wherein the electrophoresis medium comprises a gel and/or buffer liquid.

11. A capillary array for an electrophoresis apparatus comprising:

a plurality of capillaries having first aligned ends and second aligned ends;

a plurality of sample injection inlets at the first aligned ends of the capillaries; and a capillary head capable of coupling to a mounting part of the electrophoresis apparatus, wherein the second aligned ends of the plurality of capillaries are adhered to each other with adhesive, and a capillary holder having an end bundles the aligned second ends of the plurality of capillaries so that the capillary holder end, the aligned second ends of the plurality of capillaries, and the adhesive adhering the aligned second ends of the capillaries form a plane surface that will contact an electrophoresis medium which is injected into the capillaries.

12. A capillary assembly for an electrophosresis apparatus according to claim 11, wherein the plane surface formed by the capillaries, capillary holder and adhesive is an approximately mirror-finished surface.

13. A capillary assembly for an electrophosresis apparatus according to claim 11, wherein the mirror-finished surface roughness is 3.2s or less.

14. A capillary assembly for an electrophosresis apparatus according to claim 11, wherein the electrophosresis medium comprises a gel and/or a buffer liquid.

15. A capillary array for an electrophoresis apparatus comprising:

a plurality of capillaries having first aligned ends and second aligned ends;

a plurality of sample injection inlets at the first aligned ends of the capillaries; and a capillary head capable of coupling to a mounting part of the electrophoresis apparatus, wherein the capillary head comprises a capillary holder that bundles together the second aligned ends of the capillaries, the capillaries are adhered together with adhesive, the second aligned ends of the capillaries, an end of the capillary holder, and the adhesive together form a plane surface that will contact an electrophoresis medium which is injected into the capillaries, and at the plane surface the ratio of the total cross-selectional area of the capillaries in the bundled capillaries to the capillary holder internal area is 60 to 73%.

16. A capillary assembly for an electrophoresis apparatus according to claim 15, wherein the electrophoresis comprises a gel and/or a buffer liquid.

17. A capillary assembly for an electrophoresis apparatus comprising:

a plurality of capillaries having first aligned ends and second aligned ends;

a plurality of sample injection inlets at the first aligned ends of the capilliaries; and a capilliary head capable of coupling to a mounting part of a container containing an electrophoresis medium, wherein an electrophoresis medium is capable of being provided to the capilliaries via the second aligned ends, the second aligned ends of the capilliaries are adhered to each other with adhesive, the capilliary head has a capilliary holder bundling together the second aligned ends of the capillaries, the capiliary holder is sealed and fixed using a sealing peg and a tightening knob, and the hardness of each of the capilliary holder, of the tightening knob, and of the mounting part is greater than the hardness of the sealing peg.

18. A capillary assembly for an electrophoresis apparatus according to claim 17, wherein the capillary holder contacts the sealing peg to from a first contact area, the sealing peg contacts the tightening knob to form a second contact area, and the first contact area is larger than the second contact area.

19. A capillary assembly for an electrophoresis apparatus according to claim 17, wherein the electrophoresis medium comprises a gel and/or buffer liquid.

20. A capillary assembly for an electrophoresis apparatus according to claim 17, wherein the capilliary holder is longer than the tightening knob.

21. A capillary assembly for an electrophoresis apparatus comprising:

a plurality of capilliaries having first aligned ends and second aligned ends;

a plurality of sample injection inlets at the first aligned end of the capilliaries; and a capilliary head capable of coupling to a mounting part of a container containing an electrophoresis medium, wherein the electrophoresis medium is capable of being provided to the capilliaries via the second aligned ends, the second aligned ends of the plurality of capilliaries are adhered to each other with adhesive, the capilliary head has a capilliary holder bundling together the second aligned ends of the capillaries, the capilliary holder is sealed and fixed using a sealing peg and a tightening knob, and wherein the capilliary holder contacts the sealing peg to form a first contact area, the sealing peg contacts the tightening knob to form a second contact area, and the first contact area is larger than the second contact area.

22. A capilliary assembly for an electrophoresis apparatus according to claim 21, wherein the hardness of each of the capilliary holder, of the tightening knob, and of the mounting part is greater than the hardness of the sealing peg.

23. A capilliary assembly for an electrophoresis apparatus according to claim 21, wherein the capilliary holder is longer than the tightening knob.

24. A capilliary assembly for an electrophoresis apparatus according to claim 21, wherein the electrophoresis medium comprises a gel and/or buffer liquid.

25. A capilliary assembly for an electrophoresis apparatus comprising:
    a plurality of capilliaries having first aligned ends and second aligned ends;
    a plurality of sample injection inlets at the first aligned ends of the capilliaries; and
    a capilliary head coupled to a mounting part of a container containing an electrophoresis apparatus,
    wherein the electrophoresis medium is capable of being provided to the capilliaries via the second aligned ends, and
    the capilliary head comprises
        a capilliary holder bundling together the second aligned ends of the capilliaries,
        a sealing peg, and
        a tightening knob fixing the capilliary head to the mounting part by rotating the tightening knob without rotating the sealing peg.

26. A capilliary assembly for an electrophoresis apparatus according to claim 25, wherein the capilliary holder contact the sealing peg to form a first contact area, the sealing peg contacts the tightening knob to form a second contact area, and first contact area is larger than the second contact area.

27. A capilliary assembly for an electrophoresis apparatus according to claim 25, wherein the hardness of each of the capilliary holder, of the tightening knob, and of the mounting part is greater than the hardness of the sealing peg.

28. A capilliary assembly for an electrophoresis apparatus according to claim 25, wherein the electrophoresis medium comprises a gel and/or a buffer liquid.

29. A capilliary electrophoresis apparatus comprising:
    an excitation optical system irradiating electromagnetic waves to a plurality of capilliaries;
    a detection optical system detecting fluorescent lights from the capilliaries;
    a container, having a mounting for fluid communication, for holding an electrophoresis medium that is injected into the capilliaries; and
    a capilliary assembly which comprises:
        the plurality of capilliaries having first aligned ends and second aligned ends;
        a plurality of sample injection inlets at the first aligned ends of the capillaries; and
        a capilliary head capable of coupling to the mounting part, wherein the second aligned ends of the plurality of capilliaries are adhered to each other with adhesive, and a capilliary holder having an end bundles the second aligned ends of the plurality of capilliaries so that the capilliary holder end, the second aligned ends of the plurality of capilliaries, and the adhesive adhering the second aligned ends of the capilliaries form a plane surface that will contact the electrophoresis medium.

30. A capilliary electrophoresis apparatus according to claim 29, wherein the plane surface formed by the capilliaries, capilliary holder and adhesive is an approximately mirror-finish surface.

31. A capilliary electrophoresis apparatus according to claim 29, wherein the electrophoresis medium comprises a gel and/or a buffer liquid.

32. A capilliary electrophoresis apparatus according to claim 30, wherein the mirror-finished surface roughness is 3.2s or less.

33. A capilliary electrophoresis apparatus comprising:
    an excitation optical system irradiating electromagnetic waves to a plurality of capilliaries;
    a detection optical system detecting fluorescent lights from the capilliaries;
    a container, fluidly communicating with a mounting part, for holding an electrophoresis medium that is injected into the capilliaries; and
    a capilliary assembly which comprises:
        the plurality of capilliaries having first aligned ends and second aligned ends;
        a plurality of sample injection inlets at the first aligned ends of the capillaries; and
        a capilliary head capable of coupling to the mounting part, wherein the capilliary head comprises a capilliary holder that bundles together the second aligned ends of the capilliaries,
        the capilliaries are adhered together with adhesive,
        the second aligned ends of the capilliaries, an end of the capilliary holder, and the adhesive together form a plane surface that will contact the electrophoresis medium which is injected into the capilliaries, and
        at the plane surface the ratio of the total cross-sectional area of the capillaries in the bundled capillaries to the capillary holder internal area is 60 to 73%.

34. A capillary electrophoresis apparatus according to claim 33, wherein the electrophoresis medium comprises a gel and/or a buffer liquid.

35. A capillary electrophoresis apparatus comprising:
    an excitation optical system irradiating electromagnetic waves to a plurality of capillaries;
    a detection optical system detecting fluorescent lights from the capillaries;
    a container, fluidly communicating with a mounting part, for holding an electrophoresis medium that is injected into the capillaries; and
    a capillary assembly which comprises:
        the plurality of capillaries having first aligned ends and second aligned ends;
        a plurality of sample injection inlets at the first aligned ends of the capillaries; and
        a capillary head capable of coupling to the mounting part, wherein the electrophoresis medium is capable of being provided to the capillaries via the second aligned ends;
        the second aligned ends of the capillaries are adhered to each other with adhesive;
        the capillary head has a capillary holder bundling together the second aligned ends of the capillaries,
        the capillary holder is sealed and fixed using a sealing peg and a tightening knob, and
        the hardness of each of the capillary holder, the tightening knob, and the mounting part is greater than the hardness of the sealing peg.

36. A capillary electrophoresis apparatus according to claim 35, wherein the capillary holder contacts the sealing peg to form a first contact area, the sealing peg contacts the tightening knob to form a second contact area, and the first contact area is larger than the second contact area.

37. A capillary electrophoresis apparatus according to claim 35, wherein the capillary holder is longer than the tightening knob.

38. A capillary electrophoresis apparatus according to claim 35, wherein the electrophoresis medium comprises a gel and/or a buffer liquid.

39. A capillary electrophoresis apparatus comprising:

an excitation optical system irradiating electromagnetic waves to a plurality of capillaries;

a detection optical system detecting fluorescent lights from the capillaries;

a container, fluidly communicating with a mounting part, for holding an electrophoresis medium that is injected into the capillaries; and a capillary assembly which comprises:

the plurality of capillaries having first aligned ends and second aligned ends;

a plurality of sample injection inlets at the first aligned ends of the capillaries; and a capillary head capable of coupling to the mounting part, wherein the electrophoresis medium is capable of being provided to the capillaries via the second aligned ends, and the capillary head comprises a capillary holder bundling together the second aligned ends of the capillaries, a sealing peg, and a tightening knob fixing the capillary head to the mounting part by rotating the tightening knob without rotating the sealing peg.

40. A capillary electrophoresis apparatus according to claim 39, wherein the capillary holder contacts the sealing peg to form a first contact area, the sealing peg contacts the tightening knob to form a second contact area, and the first contact area is larger than the second contact area.

41. A capillary electrophoresis apparatus according to claim 39, wherein the hardness of each of the capillary holder, the tightening knob, and the mounting part is greater than the hardness of the sealing peg.

42. A capillary electrophoresis apparatus according to claim 39, wherein the electrophoresis medium comprises a gel and/or a buffer liquid.

* * * * *